United States Patent
Kim et al.

(10) Patent No.: US 12,043,644 B2
(45) Date of Patent: *Jul. 23, 2024

(54) BENZIMIDAZOLE DERIVATIVES, PREPARATION METHOD THEREOF AND USE THEREOF AS ANTI-CANCER AGENT OR ANTI-VIRUS AGENT COMPRISING THE SAME

(71) Applicant: BIOMETRIX TECHNOLOGY INC, Chuncheon-si (KR)

(72) Inventors: Junghun Kim, Seoul (KR); Keumsoo Song, Chuncheon-si (KR); Taisun Kim, Chuncheon-si (KR)

(73) Assignee: BIOMETRIX TECHNOLOGY INC, Chuncheon-si (KR)

( * ) Notice: Subject to any disclaimer, the term of this patent is extended or adjusted under 35 U.S.C. 154(b) by 711 days.

This patent is subject to a terminal disclaimer.

(21) Appl. No.: 17/051,154

(22) PCT Filed: Sep. 29, 2020

(86) PCT No.: PCT/KR2020/013371
§ 371 (c)(1),
(2) Date: Dec. 2, 2020

(87) PCT Pub. No.: WO2021/261663
PCT Pub. Date: Dec. 30, 2021

(65) Prior Publication Data
US 2021/0395289 A1 Dec. 23, 2021

(30) Foreign Application Priority Data
Jun. 23, 2020 (KR) .................... 10-2020-0076802

(51) Int. Cl.
*C07H 17/02* (2006.01)
*A61P 35/00* (2006.01)

(52) U.S. Cl.
CPC .............. *C07H 17/02* (2013.01); *A61P 35/00* (2018.01)

(58) Field of Classification Search
CPC ..... C07H 17/02; A61K 31/7052; A61P 35/00; A61P 31/12
USPC ......................................................... 514/43
See application file for complete search history.

(56) References Cited

U.S. PATENT DOCUMENTS

| | | |
|---|---|---|
| 6,455,506 B1 | 9/2002 | Townsend et al. |
| 10,533,033 B2 | 1/2020 | Jiang et al. |
| 10,988,500 B2 | 4/2021 | Jiang et al. |
| 2018/0009833 A1 | 1/2018 | Jiang et al. |
| 2020/0109160 A1 | 4/2020 | Zi-hua et al. |

FOREIGN PATENT DOCUMENTS

| | | |
|---|---|---|
| CN | 1272113 A | 11/2000 |
| CN | 106892948 A | 6/2017 |
| CN | 107531736 A | 1/2018 |
| JP | 04-007867 A | 1/1992 |
| JP | 08-001833 A | 1/1996 |
| JP | 09-025337 A | 1/1997 |
| JP | 11-006424 A | 1/1999 |
| JP | 2018-509384 A | 4/2018 |
| WO | WO 98/51304 | 11/1998 |
| WO | WO 98/56761 | 12/1998 |
| WO | WO 2005/058870 A1 | 6/2005 |
| WO | WO 2005/100373 A2 | 10/2005 |
| WO | WO2016/109880 A1 * | 7/2016 ............. A61P 35/00 |
| WO | WO 2016 109880 A1 | 7/2016 |

OTHER PUBLICATIONS

El-Nezhawy, A.O.H. et al., Structure-Based Design of Benzimidazole Sugar Conjugates: Synthesis, SAR and In Vivo Anti-inflammatory and Analgesic Activities, Medicinal Chemistry, 2009, 5, 6, p. 558-569.
Kharitonova, M.I. et al., "Benzimidazole nucleosides antiviral and antitumour activities and methods of synthesis", Russian Chemical Reviews, 2018, 87, 11, p. 1111-1138.
Smellie, I.A.S. et al., "Synthesis of 2-pyranosyl benzothiazoles, benzimidazoles and benzoxazoles via nucleophilic addition reactions of pyranosyl nitrile oxides", Tetrahedron, 66, 35, p. 7155-7160.
Search Report issued on Mar. 17, 2021 for Application No. PCT/KR2020/013371, 5 pages.
Korean Office Action for Application No. 10-2020-0076802, dated Feb. 3, 2022, and English translation, 8 pages.
Gokhale, et al., "Glycosylation of Aromatic Amines I: Characterization of Reaction Products and Kinetic Scheme," Research Article, AAPS PharmSciTech, vol. 10, No. 2, Jun. 2009, pp. 317-328.
Chu, et al., "Potent Inhibition of Tubulin Polymerisation and Proliferation of Paclitaxel- resistant 1A9PTX22 Human Ovarian Cancer Cells by Albendazole," Anticancer Research 29, 2009, pp. 3791-3796.

(Continued)

*Primary Examiner* — Ganapathy Krishnan
(74) *Attorney, Agent, or Firm* — Lewis Roca Rothgerber Christie LLP

(57) ABSTRACT

The present invention provides a benzimidazole derivative represented by the following Chemical Formula 1, a preparation method thereof, and use thereof as an anticancer or anti-virus agent:

[Chemical Formula 1]

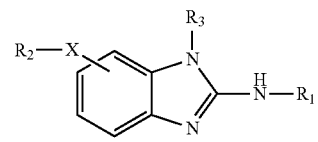

wherein, $R_1$, $R_2$, $R_3$ and X are as defined in the detailed description and the claims.

1 Claim, 8 Drawing Sheets

(56) References Cited

OTHER PUBLICATIONS

Slater, et al., "Studies On Succinate-Tetrazolium Reductase Systems III. Points of Coupling of Four Different Tetrazolium Salts," Biochimica Et Biophysica Acta 77, BBA 12288, 1963, pp. 383-393.
Thaker, et al., "Viral hijacking of cellular metabolism," BMC Biology (2019) 17:59, 15 pages.
Alley, et al., "Feasibility of Drug Screening with Panels of Human Tumor Cell Lines Using a Microculture Tetrazolium Assay[1]," Cancer Research 48, Feb. 1, 1988, pp. 589-601.
Aguayo-Ortiz, et al., "Structure-based approaches for the design of benzimidazole-2-carbamate derivatives as tubulin polymerization inhibitors," Research Article, 2016, 19 pages, doi: 10.1111/cbdd.12926.
Zhang, et al., "Anthelmintic drug albendazole arrests human gastric cancer cells at the mitotic phase and induces apoptosis," Experimental and Therapeutic Medicine 13: 2017, pp. 595-603.
Hong, "Albendazole and Praziquantel: Review and Safety Monitoring in Korea," Infection & Chemotherapy 2018; Review Article, 50(1): pp. 1-10.
Fontaine, et al., "Dengue Virus Induces and Requires Glycolysis for Optimal Replication," Journal of Virology, Feb. 2015 vol. 89 No. 4, pp. 2358-2366.
Quan, et al., "Glucose-modification of cisplatin to facilitate cellular uptake, mitigate toxicity to normal cells, and improve anti-cancer effect in cancer cells," Journal of Molecular Structure, 2019, 12 pages.
Noch, et al., "Oncogenic Viruses and Tumor Glucose Metabolism: Like Kids in a Candy Store," NIH Public Access, Mol Cancer Ther. Jan. 2012; 11(1): 14-23, 16 pages.
Dogra, et al., "Fenbendazole acts as a moderate microtubule destabilizing agent and causes cancer cell death by modulating multiple cellular pathways," Scientific Reports (2018) 8:11926, pp. 1-15.
Van De Loosdrecht, et al., "A tetrazolium-based colorimetric MTT assay to quantitate human monocyte mediated cytotoxicity against leukemic cells from cell lines and patients with acute myeloid leukemia," Journal of Immunological Methods 174 (1994) pp. 311-320.
Kohio, et al., "Glycolytic control of vacuolar-type ATPase activity: A mechanism to regulate influenza viral infection," Virology, vol. 444, Issues 1-2, Sep. 2013, pp. 301-309.
Mikic, et al., "Impossibility of the treatment of inoperable liver multicystic echinococcosis due to adverse reactions to antihelminitics," Vojnosanitetski pregled. Military-medical and pharmaceutical review 66(10): pp. 833-839.
Notice of Reasons for Refusal for Japanese Application No. 2020-560771, dated Jul. 25, 2023, 3 pages, and English translation, 4 pages.
Adekola, K. et al., "Glucose transporters in cancer metabolism," Current Opinion in Oncology, 2012, vol. 24, No. 6, p. 650-654.
Japanese Office Action for Japanese Patent Application No. 2020-560771, dated Oct. 18, 2022, 3 pages.
Chinese Office Action for Application No. 202080002572.7, dated Jan. 23, 2024, 12 pages.
"Preparation of glycosyl benzimidazole and isoxazole derivatives and their antitumor activities," May 13, 2017, with English abstract, 102 pages.
Shen, Chao et al., "A concise, efficient synthesis of sugar-based benzothiazoles through chemoselective intramolecular C-S coupling," Chem. Sci., 2012, 3, 2388, 11 pages.
Silverman, Richard B., "The Organic Chemistry of Drug Design and Drug Action," Second Edition, 2007, 5 pages, and English Abstract, 3 pages.

\* cited by examiner

FIG. 5

| Structure | Product name |
|---|---|
| [structure] | 1H NMR (400 MHz, DMSO-d6): δ = 11.62 (s, 1H), 7.15 (s, 1H), 7.06 (d, J = 7.49Hz, 1H), 6.94 (d, J = 7.50Hz, 1H), 6.80 (s, 1H), 5.04 (d, J = 7.2 Hz, 1H), 3.99-3.90 (m, 1H), 3.80-3.71 (m, 1H), 3.62-3.32 (m, 4H), 2.58 (t, J = 7.14, 4.48Hz, 2H), 1.54 (m, 2H), 0.95 (t, J = 7.96Hz, 3H). |
| [structure] | 1H NMR (400 MHz, DMSO-d6): δ = 11.62 (s, 1H), 7.15 (s, 1H), 7.06 (d, J = 7.49Hz, 1H), 6.94 (d, J = 7.50Hz, 1H), 6.80 (s, 1H), 5.33 (d, 1H), 5.24 (d, 1H), 5.08 (t, 1H) 3.89-3.94 (s, 2H), 3.99-3.91 (m, 1H), 3.80-3.74 (m, 1H), 3.62-3.33 (m, 4H), 2.57 (t, J = 7.14, 4.48Hz, 2H), 1.53 (m, 2H), 0.94 (t, J = 7.96Hz, 3H). |
| [structure] | 1H NMR (400 MHz, DMSO-d6): δ = 11.62 (s, 1H), 7.15 (s, 1H), 7.06 (d, J = 7.49Hz, 1H), 6.94 (d, J = 7.50Hz, 1H), 6.80 (s, 1H), 5.04 (d, J = 7.2 Hz, 1H), 3.99-3.90 (m, 1H), 3.80-3.71 (m, 1H), 3.62-3.32 (m, 4H), 2.58 (t, J = 7.14, 4.48Hz, 2H), 1.54 (m, 2H), 0.95 (t, J = 7.96Hz, 3H). |
| [structure] | 1H NMR (400 MHz, DMSO-d6): δ = 11.62 (s, 1H), 7.15 (s, 1H), 7.06 (d, J = 7.49Hz, 1H), 6.94 (d, J = 7.50Hz, 1H), 6.80 (s, 1H), 5.04 (d, J = 7.2 Hz, 1H), 3.99-3.90 (m, 1H), 3.80-3.71 (m, 1H), 3.62-3.32 (m, 4H), 2.58 (t, J = 7.14, 4.48Hz, 2H), 1.54 (m, 2H), 0.95 (t, J = 7.96Hz, 3H). |

| Structure | Product name |
|---|---|
|  | 1H NMR (400 MHz, DMSO-d6): δ = 12.1 (s, 1H), 11.0 (s, 1H), 7.23~7.02 (m, J = Hz, 8H) 5.04 (d, J = 7.2 Hz, 1H), 3.99–3.90 (m, 1H), , 3.80–3.71 (m, 1H), 3.62–3.32 (m, 4H) |
|  | 1H NMR (400 MHz, DMSO-d6): δ = 12.1 (s, 1H), 11.0 (s, 1H), 7.23~7.02 (m, J = Hz, 8H), 5.04 (d, J = 7.2 Hz, 1H), 3.88-3.92 (s, 2H), 3.99–3.90 (m, 1H), , 3.80–3.71 (m, 1H), 3.62–3.32 (m, 4H) |
|  | 1H NMR (400 MHz, DMSO-d6): δ = 12.1 (s, 1H), 11.0 (s, 1H), 7.23~7.02 (m, J = Hz, 8H), 5.04 (d, J = 7.2 Hz, 1H), 3.25–3.33 and 3.54–3.62 (m, 2H), 3.70–4.15(m, 4H) |
|  | 1H NMR (400 MHz, DMSO-d6): δ = 12.1 (s, 1H), 11.0 (s, 1H), 7.23~7.02 (m, J = Hz, 8H), 5.04 (d, J = 7.2 Hz, 1H), 3.25–3.33 and 3.54–3.62 (m, 2H), 3.70–4.15(m, 4H) |

FIG. 7

| Structure | Product name |
|---|---|
| (structure) | 1H NMR (400 MHz, DMSO-d6): δ = 12.1 (s, 1H), 11.0 (s, 1H), 7.42~7.12 (m, J = Hz, 7H), 5.04 (d, J = 7.2 Hz, 1H), 3.99–3.90 (m, 1H), , 3.80~3.71 (m, 1H), 3.62–3.32 (m, 4H) |
| (structure) | 1H NMR (400 MHz, DMSO-d6): δ = 12.1 (s, 1H), 11.0 (s, 1H), 7.42~7.12 (m, J = Hz, 7H), 5.04 (d, J = 7.2 Hz, 1H), 3.88-3.92 (s, 2H), 3.99–3.90 (m, 1H), , 3.80–3.71 (m, 1H), 3.62–3.32 (m, 4H) |
| (structure) | 1H NMR (400 MHz, DMSO-d6): δ = 12.1 (s, 1H), 11.0 (s, 1H), 7.42~7.12 (m, J = Hz, 7H), 5.04 (d, J = 7.2 Hz, 1H), 3.25–3.33 and 3.54–3.62 (m, 2H), 3.70–4.15(m, 4H) |
| (structure) | 1H NMR (400 MHz, DMSO-d6): δ = 12.1 (s, 1H), 11.0 (s, 1H), 7.42~7.12 (m, J = Hz, 7H), 5.04 (d, J = 7.2 Hz, 1H), 3.25–3.33 and 3.54–3.62 (m, 2H), 3.70–4.15(m, 4H) |

| Structure | Product name |
|---|---|
|  | 1H NMR (400 MHz, DMSO-d6): δ = 12.1 (s, 1H), 11.0 (s, 1H), 7.44~7.20 (m, J = Hz, 8H), 5.04 (d, J = 7.2 Hz, 1H), 3.99–3.90 (m, 1H), , 3.80–3.71 (m, 1H), 3.62–3.32 (m, 4H) |
|  | 1H NMR (400 MHz, DMSO-d6): δ = 12.1 (s, 1H), 11.0 (s, 1H), 7.44~7.20 (m, J = Hz, 8H), 5.04 (d, J = 7.2 Hz, 1H), 3.88-3.92 (s, 2H), 3.99–3.90 (m, 1H), , 3.80–3.71 (m, 1H), 3.62–3.32 (m, 4H) |
|  | 1H NMR (400 MHz, DMSO-d6): δ = 12.1 (s, 1H), 11.0 (s, 1H), 7.44~7.20 (m, J = Hz, 8H), 5.04 (d, J = 7.2 Hz, 1H), 3.25–3.33 and 3.54–3.62 (m, 2H), 3.70–4.15(m, 4H) |
|  | 1H NMR (400 MHz, DMSO-d6): δ = 12.1 (s, 1H), 11.0 (s, 1H), 7.44~7.20 (m, J = Hz, 8H), 5.04 (d, J = 7.2 Hz, 1H), 3.25–3.33 and 3.54–3.62 (m, 2H), 3.70–4.15(m, 4H) |

BENZIMIDAZOLE DERIVATIVES, PREPARATION METHOD THEREOF AND USE THEREOF AS ANTI-CANCER AGENT OR ANTI-VIRUS AGENT COMPRISING THE SAME

CROSS-REFERENCE TO RELATED APPLICATION(S)

This application is a National Phase Patent Application of International Patent Application Number PCT/KR2020/013371, filed on Sep. 29, 2020, which claims priority of Korean Patent Application No. 10-2020-0076802, filed Jun. 23, 2020, the entire contents of both of which are incorporated herein by reference.

BACKGROUND OF THE INVENTION

1. Field of the Invention

The present invention relates to a novel benzimidazole derivative, a preparation method thereof, and use thereof as an anticancer or anti-virus agent.

2. Description of the Related Art

Benzimidazole is a compound in which an imidazole ring is attached to a benzene ring, and has various bioactivities and physiological actions, so it is attracting attention as a mother nucleus of various drugs. It has been reported that compounds having such a benzimidazole structure exhibit effects against various diseases depending on substituent groups. For example, it has been developed as an anti-inflammatory analgesic agent, antifungal agent, anticancer agent, anthelmitic agent, antihistamine agent, and the like.

Benzimidazole has been published in many papers as having the property of entering cells through a cell wall and inhibiting the formation of microtubules (see: *Chem Biol Drug Des.*, 2017 July; 90(1):40-51; *Scientific REPORTS*, 2018, 8:11926; and *ANTICANCER RESEARCH*, 29: 3791-3796, 2009). However, it is known that benzimidazole invades normal cells and abnormal cells (that is, cancer-expressing cells and virus-infected cells) without distinguishing them, thereby equally inhibiting the formation of microtubules in normal cells and abnormal cells.

Further, cancer cells and virus-infected cells show the property of absorbing large amounts of glucose, but microtubules are indispensably used to move GLUT channels to the cell wall, and cancer cells have been reported to produce about 1000 times more GLUT channels than normal cells (see: L. Quan et al./*Journal of Molecular Structure* 1203 (2020) 127361).

Therefore, when benzimidazole derivatives are intensively injected into cancer cells or virus-infected cells rather than normal cells to inhibit the formation of microtubules, the production of GLUT channels may be inhibit and the absorption of glucose can be blocked, and as a result, the growth of cancer cells or the growth of viruses in virus-infected cells can be significantly inhibited, whereby the body's immune system is known to attack cancer cells or virus-infected cells whose growth is inhibited as described above, thereby exhibiting an anticancer effect or an antiviral effect (see: *EXPERIMENTAL AND THERAPEUTIC MEDICINE* 13: 595-603, 2017).

However, since benzimidazole derivatives usually have low aqueous solubility and low bioabsorbability, they must be administered in high concentrations or in considerable amounts in order to efficiently inhibit the growth of cancer cells or virus growth in virus-infected cells. For this reason, it has been reported that it exhibits considerable side effects even in normal cells (see: Vojnosanit Pregl. 2008 July; 65(7):539-44, Infect Chemother 2018; 50(1):1-10).

Therefore, benzimidazole derivatives can be administered together with drugs that can improve absorption in the gastrointestinal tract (e.g., H2 receptor antagonists such as cimetidine or gastric acid secretion inhibitors), or it has been proposed to introduce a water-soluble substituent to improve the water solubility of the benzimidazole derivative itself.

For example, in Patent Document 1 (International Patent Publication WO1998/051304, published on Nov. 19, 1998) discloses that a 2-carbamate benzimidazole derivative can inhibit the growth of mammalian tumors and cancers and treat viral infections, and it can treat viral infections, but the aqueous solubility and bioabsorption rate are low as described above, and the pharmacological effect is not sufficient.

Patent Document 2 (International Patent Publication WO2005/058870, published on Jun. 30, 2005) discloses that a compound in which a substituent capable of increasing water solubility, such as a 3-hydroxypropyl group, a 2,3-dihydroxypropyl group or a 2-carboxyamide ethyl group is attached to an 2-amino group of the 1-aryl-2-aminobenzimidazole derivative is used as an inhibitor of replication of respiratory syncytial virus, but the aqueous solubility and bioabsorption rate are not sufficient.

Patent Document 3 (International Patent Publication WO1998/056761, published on Dec. 17, 1998) discloses a compound in which a pyranose ring derived from β-D-ribopyranose is substituted with a nitrogen atom at the 1-position of a benzimidazole derivative, and the use thereof in the treatment and prevention of viral infections. In the patent document, since the pyranose ring can contain 2 to 3 or more hydroxyl groups, the water solubility of the benzimidazole derivative is significantly increased, and the possibility of using it as an injection is also disclosed. However, only the derivative in which the pyranose ring is linked to the 1-position of benzimidazole is disclosed, and it can be seen that even when benzimidazole contains a 2-amino group, a reaction pathway that avoids the reaction with the 2-amino group is adopted.

Among these benzimidazole derivatives, as 2-aminobenzimidazole derivatives such as albendazole, fenbendazole, mebendazole, flubendazole, etc., known as anthelmintic agents, are known to exhibit surprising anticancer effects, and are receiving new interest. However, interest is also being given to ways to improve their low water solubility and bioavailability.

Albendazole and fenbendazole, which are used as anthelmintic agents, are benzimidazole carbamate-based compounds, and are absorbed through the cell wall when absorbed into cells, so that they are absorbed equally by virus-infected cells and normal cells. Therefore, it is difficult to selectively absorb these compounds only in cancer cells or virus-infected cells.

On the other hand, it has already been reported in various literatures that glucose, which is an energy source of all cells, is absorbed through the GLUT channel of cells, and cells infected with viruses use a greater amount of glucose as an energy source than normal cells (see: BMC Biology (2019) 17:59), (J Virol 89:2358-2366.), (Virology. 2013; 444 (1-2):301-9). In addition, it has been reported that in order to use a larger amount of glucose as an energy source than normal cells, virus-infected cells modify the energy metabolism of host cells, activate GLUT channels than normal cells, and rapidly absorb glucose through the GLUT channel to propagate the virus (see: Mol Cancer Ther. 2012 January; 11(1): 14-23).

In conclusion, it can be seen that cancer cells and virus-infected cells absorb virus-infected cells absorb a relatively large amount of glucose-containing sugar compounds compared to normal cells or non-virus-infected cells.

In consideration of the above points, a phenomenon in which cancer cells and virus-infected cells absorb excessive amounts of sugar compounds including glucose compared to normal cells or not-infected cells is utilized in the design of new benzimidazole derivatives, and an attempt was made to develop a method that can provide such a new benzimidazole derivative at a simple process and economical cost.

SUMMARY OF THE INVENTION

An object of the present invention is to design a new benzimidazole derivative capable of solving the above-described problems, and to provide a simple and economical preparation method thereof and use thereof as an anticancer or antiviral agent.

The problem to be solved by the present invention is not limited to the above-mentioned problems, and other problems not mentioned should be clearly understood by those skilled in the art from the following description.

In order to achieve the above object, the present invention provides a novel benzimidazole-carbohydrate conjugate compound represented by the following Chemical Formula 1:

[Chemical Formula 1]

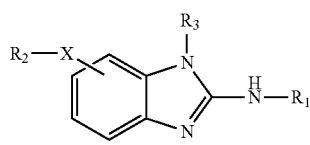

wherein, $R_1$ is a residue of a carbohydrate, and the carbohydrate may be selected from aldotetrose (e.g., erythrose, threose), aldopentose (e.g., ribose, arabinose, xylose, lixose), aldohexose (e.g., allose, altrose, glucose, mannose, glueOS, idose, galactose, tallose), ketotetrose (e.g., erythrolose), ketopentose (e.g., ribulose, xylulose), ketohexose (eg psicose, fructose, sorbose, tagatose), their isomers, oxides (CHO converts to —COOH), deoxy derivatives (—OH converted to —H, e.g., 2-deoxyribose, 2-deoxyglucose), amino sugar (—OH converted to —NH, e.g., N-acetylglucosamine, N-acetylgalactosamine), glycosides, or disaccharides thereof, preferably, may be selected from glucose, fructose, galactose, maltose or xylose;

$R_2$ and $R_3$ are the same or different and are hydrogen or a substitutable hydrocarbon group, for example, represents an alkyl group having 1 to 10 carbon atoms, an aryl group or a heteroaryl group having 3 to 10 ring atoms, and the alkyl group, the aryl group and the heteroaryl group may be substituted with halogen, cyano, hydroxy, thiol, amino, alkyl, alkyloxy, alkylamino, dialkylamino, aryl, aryloxy, arylamino, diarylamino, aryl or heteroaryl group; and X may be selected from the group consisting of —O—, —S—, —SO—, —SO$_2$—, —NH—, —N(R$_2$)—, —CH$_2$—, —CH(R$_2$)—, and —CO—.

According to one embodiment of the present invention, the benzimidazole-carbohydrate conjugate compound may be a compound represented by the following Chemical Formula 2:

[Chemical Formula 2]

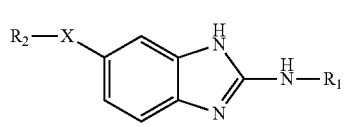

wherein, $R_1$, $R_2$ and X are the same as defined above.

According to one embodiment of the present invention, in Chemical Formula 1 or 2, the —NH—$R_1$ moiety may have one of the following structures:

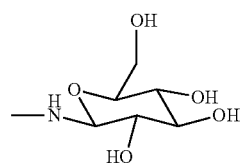

(2-Aminoglucose residue)

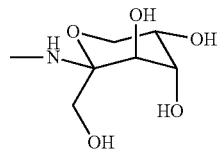

(2-Amino fructose residue)

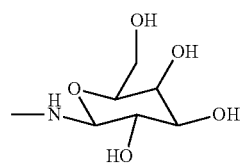

(2-Aminogalactose residue)

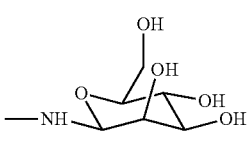

(2-Aminomannose residue).

According to one embodiment of the present invention, in the Chemical Formula 1 or 2, the benzimidazole moiety can have any one of the following structures:

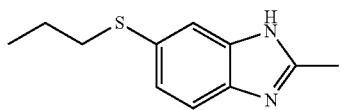

(Alvedazole residue from which 2-carbamate has been removed)

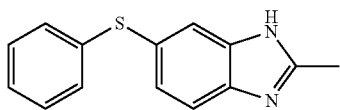 [SMILES: Cc1nc2ccc(Sc3ccccc3)cc2[nH]1]

(2-Fenbendazole residue from which carbamate has been removed)

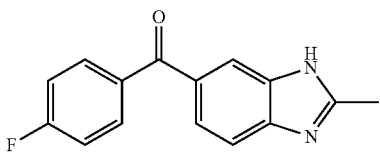 [SMILES: Cc1nc2ccc(C(=O)c3ccc(F)cc3)cc2[nH]1]

(2-Flubendazole from which carbamate has been removed)

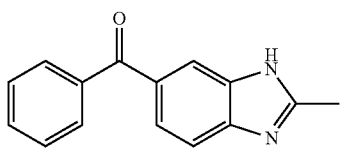

(2-Mebendazole from which carbamate has been removed).

According to one embodiment of the present invention, the benzimidazole-carbohydrate conjugate compound may be selected from the following compounds:

Alfendazole-D-carbohydrate conjugate compound:
6-(propylthio)-1H-benzoimidazol-2-aminoglucose,
6-(propylthio)-1H-benzoimidazol-2-aminofructose,
6-(propylthio)-1H-benzoimidazol-2-aminogalactose, and
6-(propylthio)-1H-benzoimidazol-2-aminomannose;

Fenbendazole-D-carbohydrate conjugate compound:
6-(phenylthio)-1H-benzoimidazol-2-aminoglucose,
6-(phenylthio)-1H-benzoimidazol-2-aminofructose,
6-(phenylthio)-1H-benzoimidazol-2-aminogalactose, and
6-(phenylthio)-1H-benzoimidazol-2-aminomannose;

Flubendazole-D-carbohydrate conjugate compound:
6-(4-fluorobenzoyl)-1H-benzoimidazol-2-aminoglucose,
6-(4-fluorobenzoyl)-1H-benzoimidazol-2-aminofructose,
6-(4-fluorobenzoyl)-1H-benzoimidazol-2-aminogalactose, and
6-(4-fluorobenzoyl)-1H-benzoimidazol-2-aminomannose;

Mebendazole-D-carbohydrate conjugate compound:
6-benzoyl-1H-benzoimidazol-2-aminoglucose,
6-benzoyl-1H-benzoimidazol-2-aminofructose,
6-benzoyl-1H-benzoimidazol-2-aminogalactose, and
6-benzoyl-1H-benzoimidazol-2-aminomannose.

In order to achieve the above object, the present invention provides a method for preparing a benzimidazole-carbohydrate conjugate compound represented by the following Chemical Formula 1, characterized in that a carbohydrate is reacted with a 2-aminobenzimidazole compound represented by the following Chemical Formula 1a.

Specifically, according to the present invention, the benzimidazole-carbohydrate conjugate compound can be prepared by reacting an aldehyde group or a ketone group of a carbohydrate with the 2-amino group of the 2-aminobenzimidazole compound of Chemical Formula 1a to form an imine bond, and cyclizing the carbohydrate moiety:

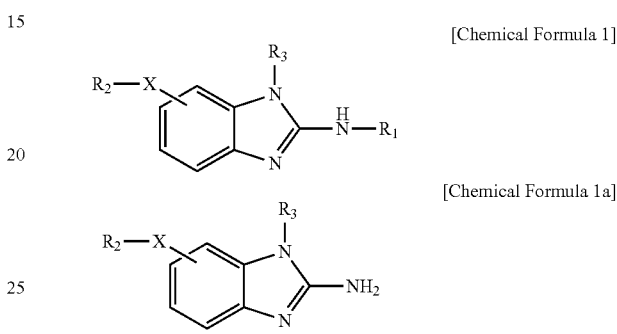

wherein, in the Chemical Formulas 1 and 1a, $R_1$, $R_2$, $R_3$ and X are as defined above.

In order to achieve the above object, the present invention provides a pharmaceutical composition containing the benzimidazole-carbohydrate conjugate compound of Chemical Formula 1.

According to one embodiment of the present invention, the benzimidazole-carbohydrate conjugate compound of Chemical Formula 1 may inhibit the formation of microtubule and inhibit the absorption of sugar compounds including carbohydrates, preferably glucose.

According to one embodiment of the present invention, the benzimidazole-carbohydrate conjugate compound of Chemical Formula 1 may exhibit anticancer or antiviral activity.

According to the present invention, a novel benzimidazole-carbohydrate conjugate compound having anticancer or antiviral activity and a method for producing the same are provided.

It should be understood that the effects of the present invention are not limited to the effects described above, but include all effects that can be inferred from the detailed description of the invention or the constitution of the invention described in the claims.

BRIEF DESCRIPTION OF THE DRAWINGS

FIG. 5 is a 1H-NMR spectrum of the albendazole-glucose conjugate compound prepared in Example 1-A.

FIG. 7 is a 1H-NMR spectrum of the flubendazole-glucose conjugate compound prepared in Example 2-A.

DETAILED DESCRIPTION OF THE INVENTION

Figure 1:
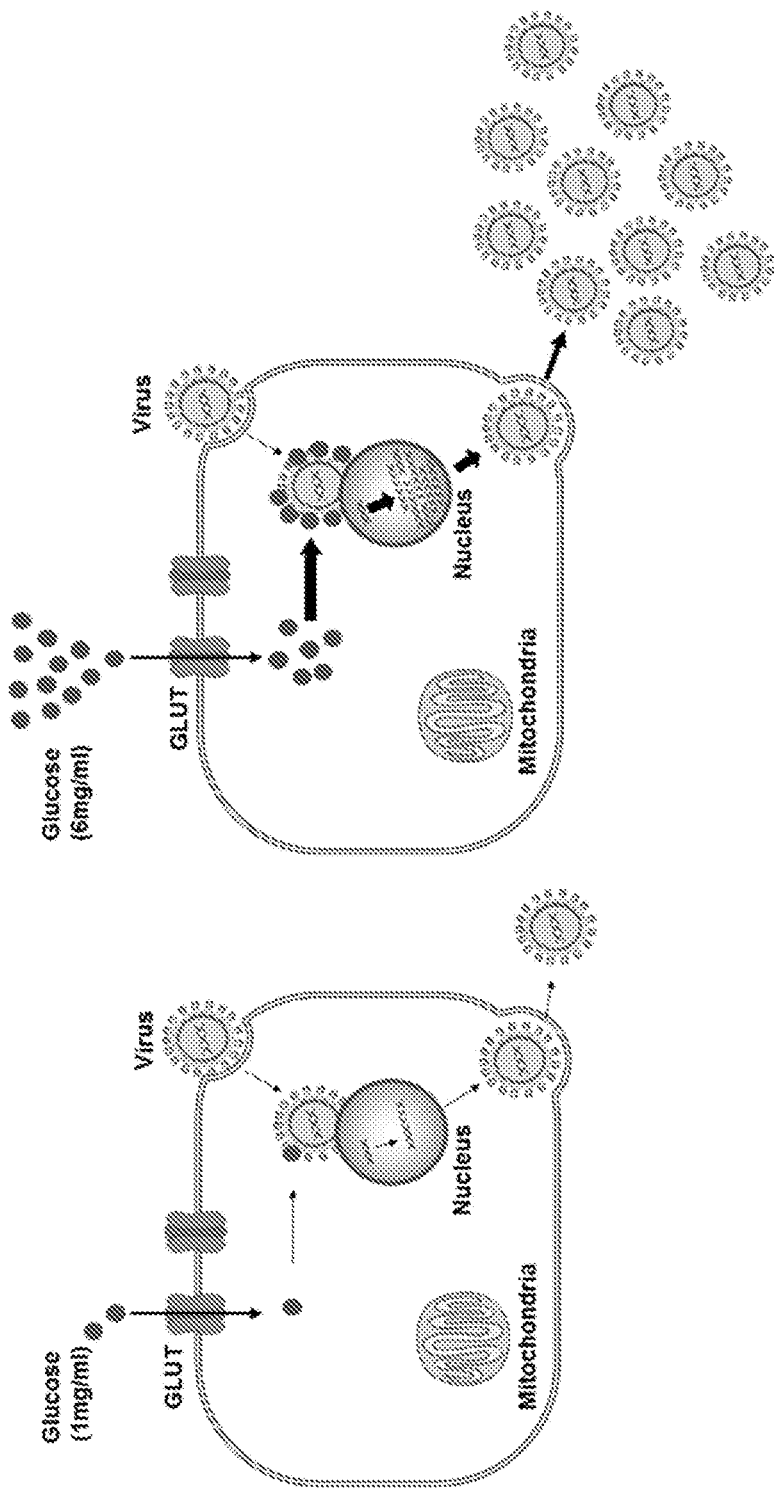
FIG. 1 is a schematic diagram conceptually showing that absorption of glucose is reduced and the growth of virus is inhibited in the GLUT channel.

Prior to a detailed description of the present invention, it should be understood that the terms and wordings used herein should not be construed to be limited to general or lexical means and the concepts of the terms may be defined to describe the invention made by the inventor(s) of the present invention in the best way, and moreover the terms and wordings should be constructed to have meanings and concepts that agree with the technical spirit of the present invention.

That is, it should be understood that the terms used herein are used only to described preferred embodiments of the present invention, but are not used to limit the contents of the present invention, and the terms are defined in consideration of various possibilities of the present invention.

Further, in the specification, a similar expression may include a plural expression unless it is indicated clearly, and a plural expression may include a singular form similarly.

Throughout the specification, when it is described that an element includes another element, it may mean that the first element may further includes any other element without excluding the other element unless a particularly contradictory description is made.

In describing the present invention, when it is determined that detailed description of a configuration that may unnecessarily disturb the gist of the present invention, for example, a known technique including a conventional technique, may be omitted.

First, terms used herein are briefly defined as follows for understanding of the present invention. However, the present invention is not limited by these meanings or definitions of terms.

The term "anticancer agent" is a substance that inhibits the growth or proliferation of cancer cells, or such drug.

The term "antiviral" refers to inhibiting the growth of cells infected with a virus, and "antiviral agent" means a substance that inhibits the growth of cells infected with a virus, or such drug.

The term "carbohydrate" is used as a generic term for organic compounds composed of sugars.

The term "inhibition of sugar compound absorption" means to inhibit the absorption or entry of sugar compounds into cells.

The term "tubulin" refers to proteins that make up microtubules present in almost all cells of an organism.

The term "microtubule" is a tube which consists of a polymer of proteins called tubulin, which constitutes a cytoskeleton and to which intracellular substances move.

The term "cell division" refers to a phenomenon in which a parent cell of an organism is divided into two cells through nuclear fission and cytoplasmic division.

The present invention will be described in more detail below.

(1) Benzimidazole-Carbohydrate Conjugate Compound

The first object of the present invention is to provide a benzimidazole-carbohydrate conjugate compound represented by the following Chemical Formula 1:

[Chemical Formula 1]

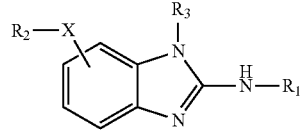

wherein, $R_1$ is a residue of a carbohydrate, and the carbohydrate is selected from aldotetrose (e.g., erythrose, threose), aldopentose (e.g., ribose, arabinose, xylose, lixose), aldohexose (e.g., allose, altrose, glucose, mannose, glueOS, idose, galactose, tallose), ketotetrose (e.g., erythrolose), ketopentose (e.g., ribulose, xylulose), ketohexose (eg psicose, fructose, sorbose, tagatose), their isomers, oxides (CHO converts to —COOH), deoxy derivatives (—OH converted to —H, e.g., 2-deoxyribose, 2-deoxyglucose), amino sugar (—OH converted to —NH, e.g., N-acetylglucosamine, N-acetylgalactosamine), glycosides, or disaccharides thereof, preferably, is selected from glucose, fructose, galactose, maltose or xylose;

$R_2$ and $R_3$ are the same or different and are hydrogen or a substitutable hydrocarbon group, for example, represents an alkyl group having 1 to 10 carbon atoms, an aryl group or a heteroaryl group having 3 to 10 ring atoms, and the alkyl group, the aryl group and the heteroaryl group may be substituted with halogen, cyano, hydroxy, thiol, amino, alkyl, alkyloxy, alkylamino, dialkylamino, aryl, aryloxy, arylamino, diarylamino, aryl or heteroaryl group; and X may be selected from the group consisting of —O—, —S—, —SO—, —SO$_2$—, —NH—, —N(R2)-, —CH$_2$—, —CH(R$_2$)—, and —CO—.

The compound of the Chemical Formula 1 may be understood as a form in which a carbohydrate residue is bound to a 2-amino group of the 2-aminobenzimidazole structure or a form in which an aminoated carbohydrate is bound to the 2-position of the benzimidazole structure.

According to one embodiment of the present invention, the benzimidazole-carbohydrate conjugate compound can be a compound represented by the following Chemical Formula 2.

[Chemical Formula 2]

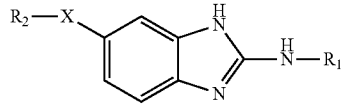

wherein, R1, R2 and X are the same as defined above.

According to one embodiment of the present invention, in Chemical Formula 1 or 2, the —NH—R$_1$ moiety may have one of the following structures:

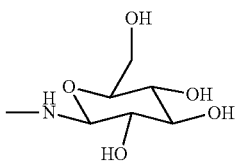

(2-Aminoglucose residue)

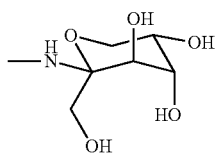

(2-Amino fructose residue)

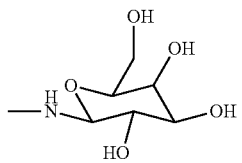

(2-Aminogalactose residue)

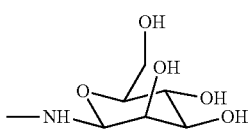

(2-Aminomannose residue)

According to one embodiment of the present invention, in the Chemical Formula 1 or 2, the benzimidazole moiety can have any one of the following structures:

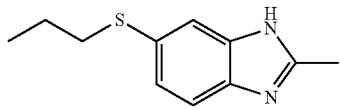

(Alvedazole residue from which 2-carbamate has been removed)

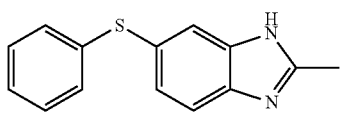 [SMILES: Cc1nc2ccc(Sc3ccccc3)cc2[nH]1]

(2-Fenbendazole residue from which carbamate has been removed)

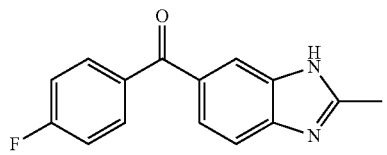 [SMILES: Cc1nc2ccc(C(=O)c3ccc(F)cc3)cc2[nH]1]

(2-Flubendazole from which carbamate has been removed)

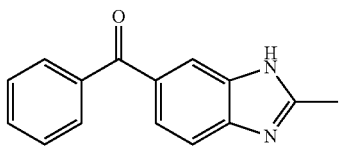 [SMILES: Cc1nc2ccc(C(=O)c3ccccc3)cc2[nH]1]

(2-Mebendazole from which carbamate has been removed)

According to one embodiment of the present invention, the benzimidazole-carbohydrate conjugate compound may be selected from the following compounds:
Alfendazole-D-carbohydrate conjugate compound:
6-(propylthio)-1H-benzoimidazol-2-aminoglucose,
6-(propylthio)-1H-benzoimidazol-2-aminofructose,
6-(propylthio)-1H-benzoimidazol-2-aminogalactose, and
6-(propylthio)-1H-benzoimidazol-2-aminomannose;
Fenbendazole-D-carbohydrate conjugate compound:
6-(phenylthio)-1H-benzoimidazol-2-aminoglucose,
6-(phenylthio)-1H-benzoimidazol-2-aminofructose,
6-(phenylthio)-1H-benzoimidazol-2-aminogalactose, and
6-(phenylthio)-1H-benzoimidazol-2-aminomannose;
Flubendazole-D-carbohydrate conjugate compound:
6-(4-fluorobenzoyl)-1H-benzimidazol-2-aminoglucose,
6-(4-fluorobenzoyl)-1H-benzimidazol-2-aminofructose,
6-(4-fluorobenzoyl)-1H-benzimidazol-2-aminogalactose, and
6-(4-fluorobenzoyl)-1H-benzimidazol-2-aminomannose;
Mebendazole-D-carbohydrate conjugate compound:
6-benzoyl-1H-benzimidazol-2-aminoglucose,
6-benzoyl-1H-benzimidazol-2-aminofructose,
6-benzoyl-1H-benzimidazol-2-aminogalactose, and
6-benzoyl-1H-benzimidazol-2-aminomannose.

In the benzimidazole-carbohydrate conjugate compound according to the present invention, the carbohydrate moiety has both a chain structure and a cyclic structure, and the chain structure is thermodynamically more stable in the pentose and hexose, but the chain structure and the cyclic structure are in equilibrium in the solution, Thus, even if only one of the two has a medicinal effect, it does not have a significant effect on the overall pharmacological effect.

(2) Method for Preparing Benzimidazole-Carbohydrate Conjugate Compound

To solve the above objects, the present invention provides a method for preparing a benzimidazole-carbohydrate conjugate compound represented by the following Chemical Formula 1, characterized in that a carbohydrate is reacted with a 2-aminobenzimidazole compound of the following Chemical Formula 1a to form an imine bond. Specifically, according to the present invention, the benzimidazole carbohydrate conjugate compound represented by Chemical Formula 1 can be prepared by reacting an aldehyde group or a ketone group of a carbohydrate with ae 2-amino group of the 2-aminobenzimidazole compound of Formula 1a to form an imine bond, and cyclizing the carbohydrate moiety.

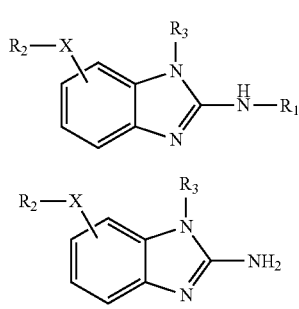

[Chemical Formula 1]

[Chemical Formula 1a]

in the Chemical Formulas 1 and 1a, $R_1$, $R_2$, $R_3$ and X are the same as defined above.

According to one embodiment of the present invention, in the 2-aminobenzimidazole compound of Formula 1a, a substituent capable of performing an imine reaction may be previously protected or blocked.

The benzimidazole-carbohydrate conjugate compound according to the present invention can be prepared by various methods, and an example of the preparation method is provided below.

As an example of preparing the benzimidazole-carbohydrate conjugate compound according to the present invention, the following Reaction Scheme 1 may be presented.

Reaction Scheme 1 shows a reaction in which a D-glucose unit is bound to the 2-amino group of 6-alkylthio-2-aminobenzimidazole, which is a precursor of albendazole or fenbendazole.

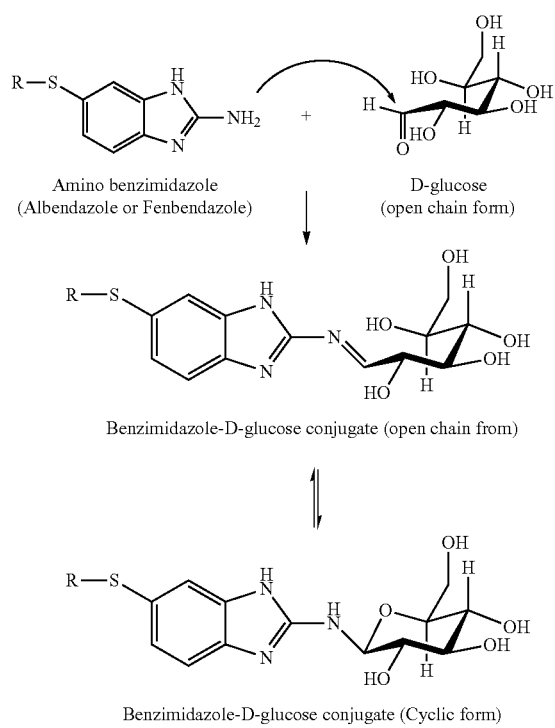

[Reaction Scheme 1]

In Reaction Scheme 1, an 2-amino group of aminobenzimidazole can be reacted with an aldehyde group of D-glucose (open chain form) to form an imine bond, and thereby, a benzimidazole-carbohydrate conjugate compound, that is, benzimidazole-D-glucose (open chain form) conjugate compound is prepared.

The benzimidazole-D-glucose (open chain form) conjugate compound may be converted into thermodynamically stable cyclic benzimidazole-D-glucose (cyclic form).

As another example of preparing the benzimidazole-carbohydrate conjugate compound according to the present invention, the following Reaction Scheme 2 can be presented.

Reaction Scheme 2 shows the reaction of binding the D-glucose unit to the 2-amino group of 6-alkylcarbonyl-2-aminobenzimidazole, which is a precursor of flubendazole or mebendazole.

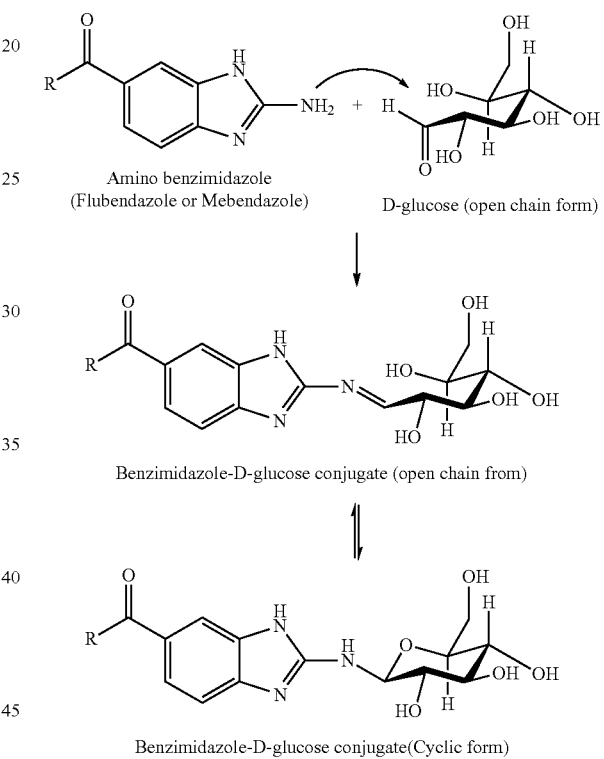

[Reaction Scheme 2]

The benzimidazole-carbohydrate conjugate compound obtained as a result of Reaction Schemes 1 and 2 can be isolated and/or purified by a conventional method, and then confirmed by a spectroscopic method (eg, 1H-NMR).

(3) Pharmacological Effects and Uses of Benzimidazole-Carbohydrate Conjugate Compounds A third object of the present invention is to provide a pharmaceutical composition or a pharmacological composition containing the benzimidazole-carbohydrate conjugate compound of Chemical Formula 1.

According to one embodiment of the present invention, the benzimidazole-carbohydrate conjugate compound of Chemical Formula 1 can exhibit a pharmacological effect of inhibiting the formation of microtubule and the absorption of carbohydrates, preferably sugar compounds including glucose, and thereby, a pharmacological composition useful for the treatment of disorders that can take advantage of intake or metabolic disorders of carbohydrates, including glucose, can be provided.

According to an embodiment of the present invention, the benzimidazole-carbohydrate conjugate compound of Formula 1 exhibits anticancer or antiviral activity, so that a pharmaceutical composition having anticancer or antiviral activity may be provided.

One of the features of the present invention is that when the fenbendazole-glucose compound (FB-G), which is one of the benzimidazole-carbohydrate conjugate compounds, is absorbed into cells in the form of glucose bound to fenbendazole, it has been designed so as to be absorbed through the GLUT channel rather than the cell wall by glucose bound to this compound. It is known that the GLUT channel is more activated in cancer cells or virus-infected cells than in normal cells. In particular, it has been reported that cancer cells form 1000 times more GLUT channels than normal cells. The benzimidazole-carbohydrate conjugate compound according to the present invention is expected to be more intensively absorbed in cancer cells and virus-infected cells in which GLUT channels are activated than in normal cells (see: L. Quan et al./Journal of Molecular Structure 1203 (2020) 127361).

According to an embodiment of the present invention, there is provided a pharmacological composition in which the benzimidazole-carbohydrate conjugate compound of Chemical Formula 1 is absorbed through a GLUT channel rather than a cell wall.

The fact that the benzimidazole-carbohydrate conjugate compound of Chemical Formula 1 according to the present invention exhibits antiviral activity can be explained as follows.

A virus is a small particle (average 0.1 um or less) that are smaller a bacteria and cannot be filtered through a bacterial filter (0.22 um), and contains only nucleic acids (DNA or RNA) and a small number of proteins as substances necessary for survival, so it is an organism that lives depending on the host, and if it is infected in the human body, it causes viral diseases.

Viruses differ in most properties from bacteria, and common antibiotics do not inhibit the growth of virus. As a therapeutic agent for diseases caused by viruses, drugs that weaken or eliminate the action of viruses that have invaded the body are called antiviral therapeutic agents. Because viral infections are difficult to treat with conventional antibiotics, they have no choice but to treat them with antiviral therapeutic agent.

Antiviral preparations currently being developed and used are drugs that inhibit the growth process of the virus, that is, inhibit the growth rate of the intracellular virus infected with virus, extremely inhibit the number of cells infected with the virus from being increased, so that the body's immune system attacks virus-infected cells and inhibits the virus's growth process below levels that can be removed.

Antiviral drugs that inhibit the growth of virus are drugs that inhibit the growth of a virus is a drug that inhibites and treats the growth of a virus by interfering with a specific step in the process of the growth of the virus in the cell.

Antiviral agents are classified into influenza therapeutic agents, herpes therapeutic agents, hepatitis B therapeutic agents, hepatitis C therapeutic agents, AIDS therapeutic agents, etc., depending on the disease group to be treated, and may be used for various diseases depending on the characteristics of the drug.

Typical antiviral drugs used as influenza therapeutic agents include Tamiflu®, Relenzarotadisk® and Peramivir®, which are used for the treatment of influenza A and influenza B virus infections.

As a herpes therapeutic agent, typical antiviral agents used for the treatment of herpes simplex virus (HSV) and varicella zoster virus (VZV) infection are Zovirax®, Valtrex®, Famciclovir®, Ocufridine®, and the like.

A therapeutic agent for hepatitis C is a drug that inhibits the growth of hepatitis C virus and delays the progression of the diseases. The combination therapy of interferon injection and ribavirin, which enhances the immune system, has been used for a long time, but relatively recently, direct acting antivirals (DAA) have been developed, and can be treated with just edible drugs, and typical examples are Viramid®, Exviera®, Sovaldi®, Daclatarvir®, and Harvoni®, and the like.

As AIDS therapeutic agents, a drug that inhibites the growth of human immunodeficiency virus (HIV) and delays the progression of the disease is to prevent the expression of resistance by using cocktail therapy in which three or more drugs are taken at the same time, and typical examples are Combivir®, Kivexa®, Trubada®, and Intelence®, and the like.

As other antiviral agents, there are drugs that inhibit the growth of viruses by enhancing or regulating human immune responses, which are substances produced and secreted by immune cells during infection, and have antiviral effect and immunomodulatory ability. Typical examples are Loferon-A®, Intron-A®, Pegasys®, and Aldara® are typical (see: Korea Pharmaceutical Information Center).

However, until now, the types and numbers of antiviral preparations that successfully treat viral infections are so poor that most viral infections are expected to be self-healing by the patient's immune function (Rider et al., 2011).

Development of drugs that inhibit the growth rate of virus-infected intracellular virus, ultimately inhibit virus-infected cells from being increased, so that the internal immune system can attack and eliminate virus-infected cells and inhibit the viral growth process below a level that can be removed, is urgently needed.

One of the advantages of the present invention is that the novel benzimidazole-carbohydrate conjugate compound according to the present invention is mainly absorbed only in cancer cells and virus-infected cells than in normal cells, and then binds to tubulin that forms microtubules, which is a known characteristic of conventional benzimidazole compound derivatives, and interferes with the formation of microtubule, inhibits cell division, whereby it is possible to effectively induce the death of cancer cells and virus-infected cells by blocking the absorption of carbohydrates containing glucose, which is a cellular energy source.

Therefore, since the novel benzimidazole-carbohydrate conjugate compound according to the present invention is absorbed intensively by cancer cells and virus-infected cells, not only it is designed to minimize toxicity to normal cells, but also it is expected to be usefully used as an anticancer and antiviral compound for the treatment of cancer and virus-infections.

Hereinafter, the present invention will be described in more detail by way of examples. However, the following examples are for more specific explanation of the present invention, and the scope of the present invention is not limited by the examples. The following examples can be appropriately modified or changed by those skilled in the art within the scope of the present invention.

EXAMPLE

Example 1-A: Albendazole-Glucose Conjugate Compound

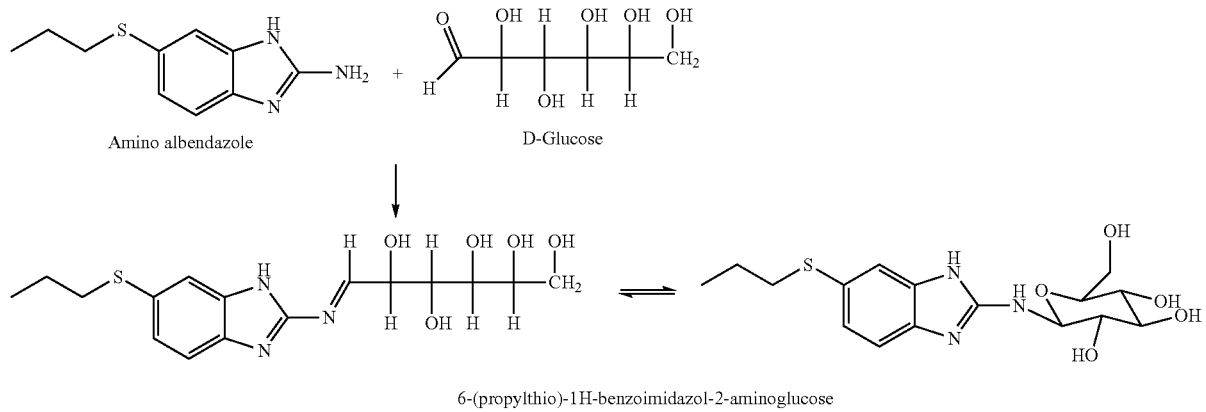

An albendazole-glucose conjugate compound was prepared according to the above reaction scheme, and the reaction procedure and conditions were referred to the methods described in documents (Gokhale, Kearney, and Kirsch, AAPS PharmSciTech, Vol. 10, No. 2, June 2009).

1.2 mM aminoalbendazole (CAS #80983-36-4) (commercially available: Albendazole amine) and 0.5 M glucose were added to a hydrochloric acid solution (pH 3.45) to prepare a reaction mixture, and reacted at 40±1° C. in a Teflon-coated rubber-stopped glass vial, and diluted with acetate buffer (0.5 M, pH 5.8) to terminate the reaction.

The solvent was removed, and purified by column chromatography using dichloromethane and 10% methanol to obtain an albendazole-glucose conjugate compound in a yield of 62%.

The product was analyzed by 1H-NMR spectrum to confirm the formation of an albendazole-glucose conjugate compound (see FIG. 5).

Example 1-B: Fenbendazole-Glucose Conjugate Compound

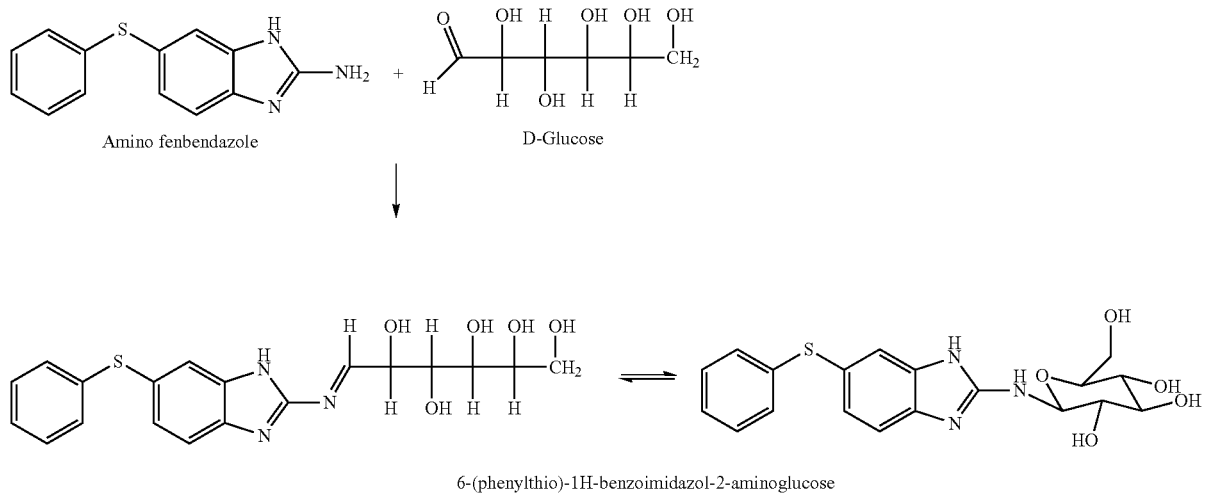

The procedure was performed in the same manner as in Example 1-A, except that aminophenbendazole (CAS #1448346-29-9) (hydrochloride form) was used instead of amino albendazole, thereby obtaining a fenbendazole-glucose conjugate compound as a benzimidazole-carbohydrate conjugate compound in a yield of 66%.

Figure 6:
FIG. 6 is a 1H-NMR spectrum of the fenbendazole-glucose conjugate compound prepared in Example 1-B.
Figure 6:
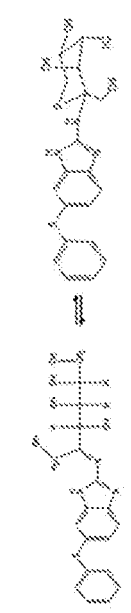
Figure 6:
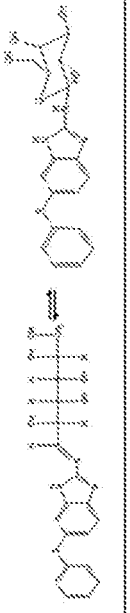
Figure 6:

The product was analyzed by 1H-NMR spectrum to confirm generation of a fenbendazole-glucose conjugate compound (see FIG. 6).

Example 2-A: Flubendazole-Glucose Conjugate Compound

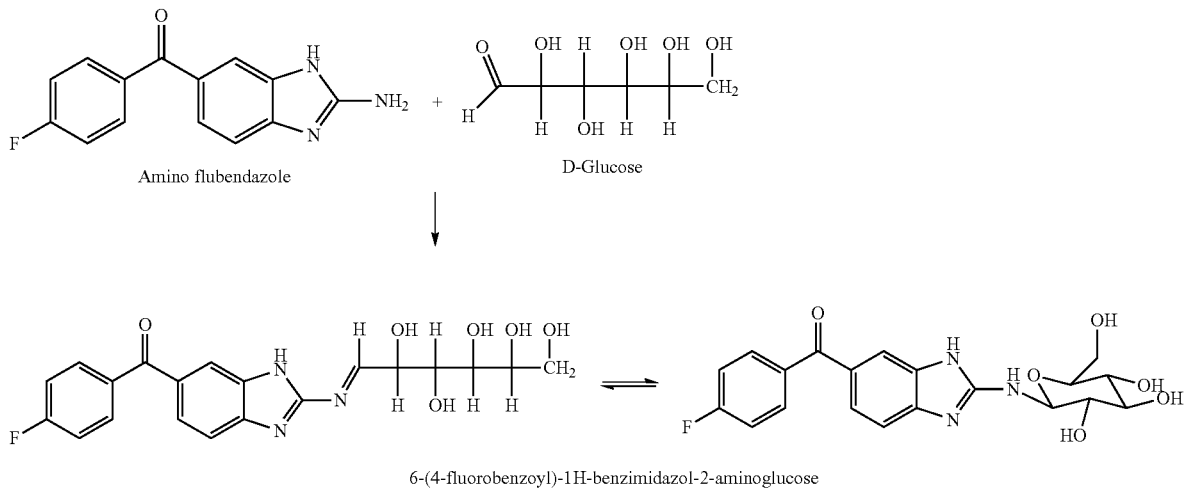

A flubendazole-glucose conjugate compound was prepared according to the reaction scheme, and the reaction procedure and conditions were referred to the methods described in documents (Gokhale, Kearney, and Kirsch, AAPS PharmSciTech, Vol. 10, No. 2, June 2009).

1.2 mM aminoflubendazole (CAS #82050-13-3) (commercial name: 2-Aminoflubendazole) and 0.5 M glucose were added to a hydrochloric acid solution (pH 3.45) to prepare a reaction mixture, reacted at 40±1° C. in a Teflon-coated rubber-stopped glass vial, and diluted with acetate buffer (0.5 M, pH 5.8) to terminate the reaction.

The solvent was removed, and purified by column chromatography using dichloromethane and 10% methanol to obtain a flubendazole-glucose conjugate compound in a yield of 68%.

The product was analyzed by 1H-NMR spectrum to confirm the formation of a flubendazole-glucose conjugate compound (see FIG. 7).

Example 2-B: Mebendazole-Glucose Conjugate Compound

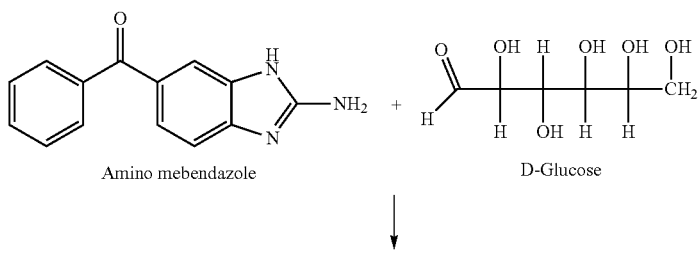

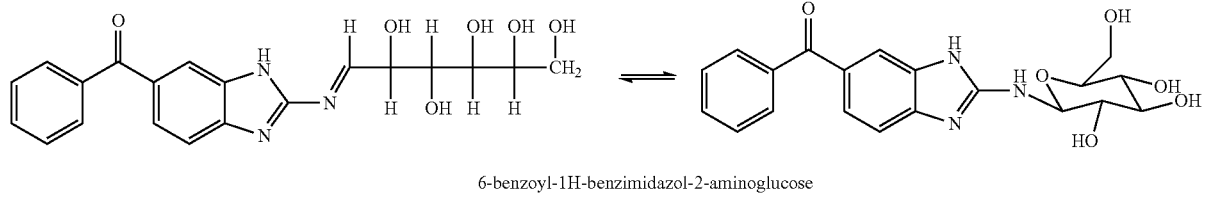

6-benzoyl-1H-benzimidazol-2-aminoglucose

The procedure was performed in the same manner as in Example 2-A, except that aminomebendazole (CAS #52329-60-9) was used instead of aminoflubendazole, thereby obtaining a mebendazole-glucose conjugate compound in a yield of 66%.

Figure 8:
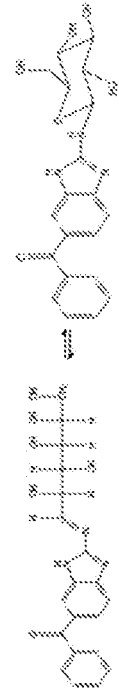
FIG. 8 is a 1H-NMR spectrum of the mebendazole-glucose conjugate compound prepared in Example 2-B.
Figure 8:
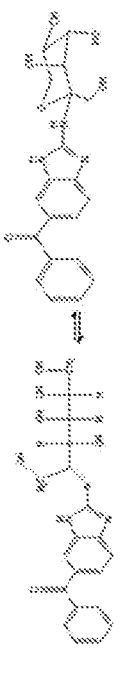
Figure 8:
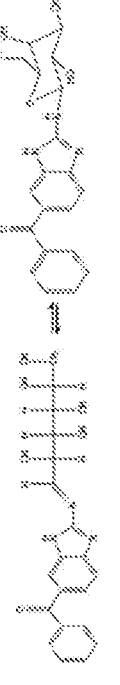
Figure 8:
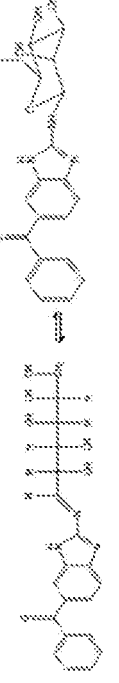

The product was analyzed by 1H-NMR spectrum to confirm the formation of a mebendazole-glucose conjugate compound (see FIG. 8).

Experimental Example 1: Cancer Cell Line Growth Inhibition Test

Human lung cancer cell line A549, cervical cancer cell line Hela, and colorectal cancer cell line HT-29 were furnished from Korea Cell Line Bank (KCLB, Seoul, Korea) and cultured in culture medium.

In a humidified cell culture incubator containing 5% $CO_2$ at 37° C. using DMEM, 10% culture flask, fetal bovine serum (FBS), 0.1 mM MEM non-essential amino acids (NEAA), 2 mM L-glutamine, and 1% penicillin-streptomycin were treated with trypsin every 2-3 days according to the guidelines provided by KCLB, and the cells were subcultured. The culture was cultured until it reached 80-90% confluence, and the cells were continuously transferred to a culture flask for a cancer cell line growth inhibition experiment.

Cancer cell lines to be tested (human lung cancer cell line A549, cervical cancer cell line Hela, and colorectal cancer cell line HT-29) were seeded in about 10000 cells per well in a 96-well plate. After 24 hours, the three compounds shown in Table 1 below were added to each well at 7 concentrations, and incubated for 72 hours.

TABLE 1

| Compound | Concentration |
| --- | --- |
| Aminophenbendazole | 0 μm, 0.1 μm, 1 μm, 10 μm, 30 μm, 50 μm, 100 μm |
| Phenbendazole-glucose conjugate | 0 μm, 0.1 μm, 1 μm, 10 μm, 30 μm, 50 μm, 100 μm |
| Doxorubicin | 0 μm, 0.1 μm, 1 μm, 10 μm, 30 μm, 50 μm, 100 μm |

In Table 1, aminophenbendazole and doxorubicin were commercially available compounds, and the fenbendazole-glucose conjugate used was the one prepared in Example 1-B.

After incubation, the medium was discarded and the cell viability was measured in each well using a WST-8 cell viability assay kit (Quanti-Max™, BIOMAX) according to the procedure instructed by the manufacturer.

The analysis utilized the principle that the dehydrogenase in living cells decomposes tetrazolium salts to produce formazan, through which living cells were quantitatively evaluated.

The reduced formazan salt is soluble in the cell culture medium and the amount of formazan is directly proportional to the number of viable cells (see: Slater, T. et al. (1963) Biochem. Biophys. Acta 77:383; van de Loosdrecht, A A, et al. J. Immunol. Methods 174: 311-320, 1994. Alley, M C, et al.; and Cancer Res. 48: 589-601, 1988.)

Figure 2:
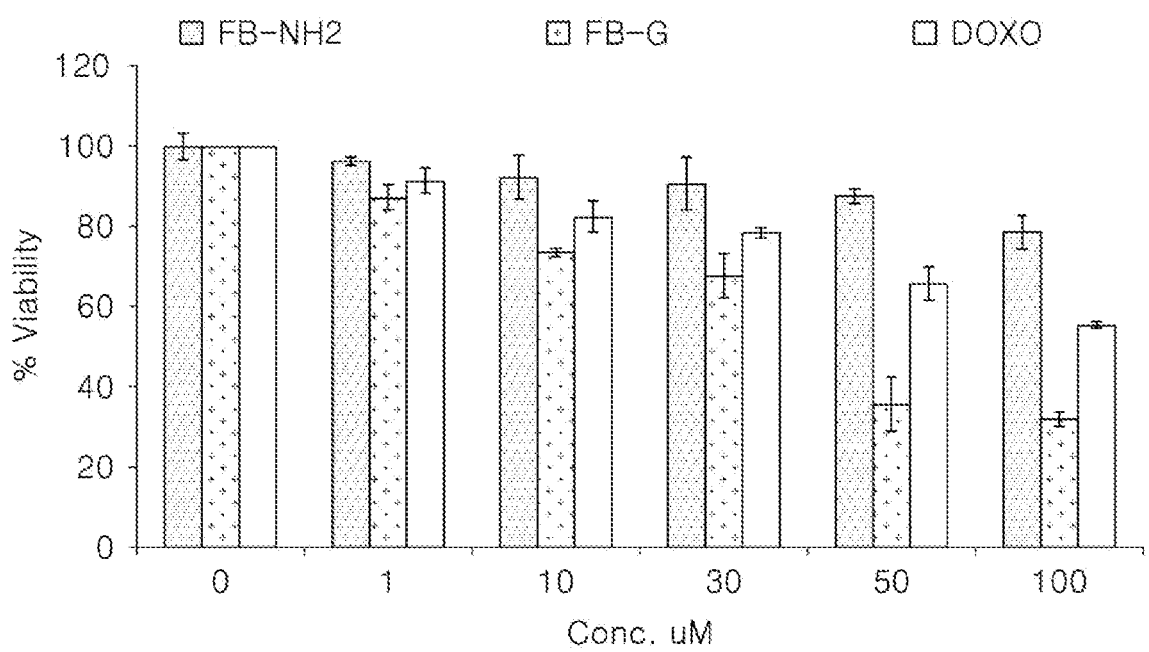
FIG. 2 is a diagram showing a growth inhibitory effect of a cancer cell line, which is a result of a toxicity test (24 hours) on a lung cancer cell line.
Figure 3:
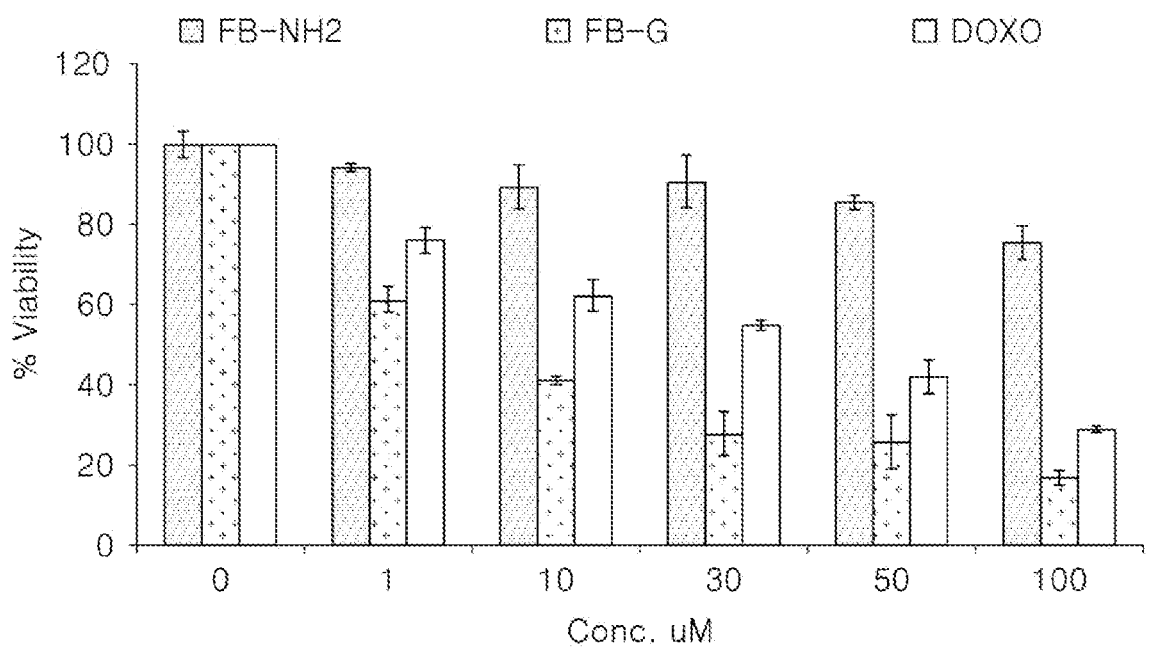
FIG. 3 is a diagram showing a growth inhibitory effect of a cancer cell line, which is a result of a toxicity test (72 hours) on a lung cancer cell line.

The results of the cancer cell line growth inhibition test performed in this test example are shown in FIGS. 2 and 3. FIG. 2 is the results of a toxicity test (24 hr) in a lung cancer cell line, and FIG. 3 is the results of a toxicity test (72 hr) in a lung cancer cell line.

Experimental Example 2: Toxicity Test in Normal Cell Line

The normal lung cell line MRC-5 and the normal colon CCD-18Co cell line were furnished from Korea Cell Line Bank (KCLB, Seoul, Korea) and cultured in culture medium.

In a humidified cell culture incubator containing 5% $CO_2$ at 37° C. using DMEM, 10% culture flask, fetal bovine serum (FBS), 0.1 mM MEM non-essential amino acids (NEAA), 2 mM L-glutamine, and 1% penicillin-streptomycin were treated with trypsin every 2-3 days according to the guidelines provided by KCLB, and the cells were subcultured. The culture was cultured until it reached 80-90% confluence, and the cells were continuously transferred to a culture flask for a cancer cell line growth inhibition experiment.

Normal cell lines (MRC-5 and CCD-18Co) were seeded in about 10000 cells per well in a 96-well plate. After 24 hours, the three compounds shown in Table 1 below were added to each well at 7 concentrations, and incubated for 72 hours.

TABLE 2

| Compound | Concentration |
| --- | --- |
| Aminophenbendazole | 0 μm, 0.1 μm, 1 μm, 10 μm, 30 μm, 50 μm, 100 μm |
| Phenbendazole-glucose conjugate | 0 μm, 0.1 μm, 1 μm, 10 μm, 30 μm, 50 μm, 100 μm |
| Doxorubicin | 0 μm, 0.1 μm, 1 μm, 10 μm, 30 μm, 50 μm, 100 μm |

Figure 4:
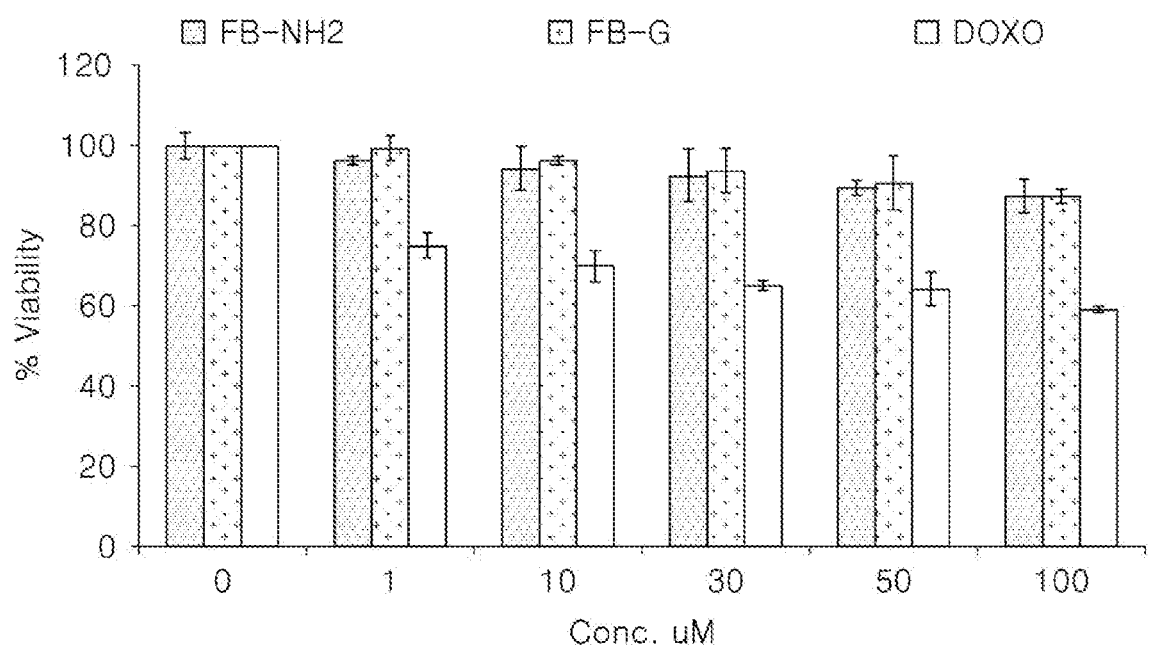
FIG. 4 is a diagram showing cell viability in a normal cell line, which is the result of a toxicity test (72 hours) in a normal cell line.

The cell viability and analysis in the normal cell line were performed in the same manner as in Test Example 1, and the results of the toxicity test (72 hours) in the normal cell line are shown in FIG. 4. Table 3 below shows that the test results of aminofenbendazole and fenbendazole-glucose conjugate compound were evaluated in comparison with doxorubicin.

TABLE 3

| | Cancer cell line growth inhibition test | Normal cell line growth inhibition test |
|---|---|---|
| Aminophenbendazole | C | A A A |
| Phenhendazole-glucose conjugate | A A A | A A A |

As can be seen from Table 3, it was confirmed that aminophenbendazole of the prior art has significantly better normal cell line toxicity test results than doxorubicin (AAA), but cancer cell line growth inhibition test result was normal (C), whereas the phenbendazole-glucose conjugate according to the present invention is significantly superior to doxorubicin in both the cancer cell line growth inhibition test and the normal cell line toxicity test (AAA).

Although specific examples of the novel benzimidazole derivative according to the present invention, a method for preparing the same, and its use as an anticancer agent or an antiviral agent have been described so far, it would be apparent that various modifications can be made to the invention within the scope of the present invention.

Therefore, the scope of the present invention should not be defined only by the above-described embodiment, but must be defined not only by the claims described later but also by something equivalent to the scope of claims.

That is, it must be understood that the above-described embodiments are exemplary in all respects and is not limiting, and the scope of the present invention is specified in the claims described below rather than the detailed description. The meaning and scope of the claims and all modified or changed forms derived from the equivalent concept shall be construed as being included in the scope of the invention.

INDUSTRIAL APPLICABILITY

The present invention is available in the pharmaceutical, medical and health industries.

What is claimed is:

1. A pharmaceutical composition comprising a benzimidazole-carbohydrate conjugate compound having anticancer or antiviral activity as an active ingredient, the benzimidazole-carbohydrate conjugate compound being represented by the following Chemical Formula 1:

Chemical Formula 1

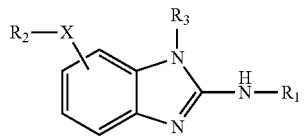

wherein the —NH—$R_1$ moiety has a structure selected from the group consisting of:

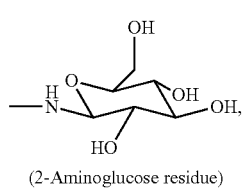

(2-Aminoglucose residue)

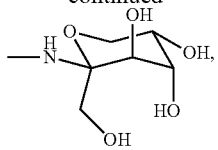

(2-Amino fructose residue)

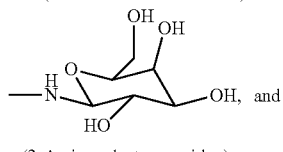

(2-Aminogalactose residue)

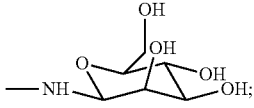

(2-Aminomannose residue)

and wherein $R_2$-X is selected from the group consisting of:

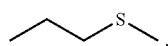

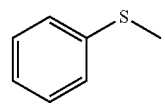

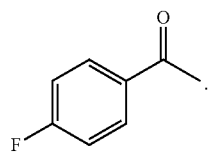

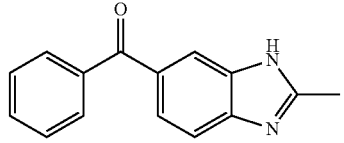

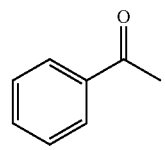

wherein $R_3$ is H.

* * * * *